(12) United States Patent
Pfirrmann et al.

(10) Patent No.: US 6,488,912 B1
(45) Date of Patent: Dec. 3, 2002

(54) TREATMENT OF DENTOALVEOLAR INFECTIONS WITH TAUROLIDINE AND/OR TAURULTAM

(75) Inventors: Rolf Wilhelm Pfirrmann, Lucerne (CH); Peter Geistlich, Stanstaad (CH)

(73) Assignee: Ed. Geistlich Soehne AG fuer Chemische Industrie, Wolhusen (CH)

( * ) Notice: Subject to any disclaimer, the term of this patent is extended or adjusted under 35 U.S.C. 154(b) by 772 days.

(21) Appl. No.: 09/345,744

(22) Filed: Jul. 1, 1999

Related U.S. Application Data

(63) Continuation of application No. 08/770,127, filed on Dec. 19, 1996, now abandoned, which is a continuation of application No. 08/374,722, filed as application No. PCT/GB93/01607 on Jul. 29, 1993, now abandoned.

(30) Foreign Application Priority Data

Jul. 30, 1992 (GB) .............................. 9216155

(51) Int. Cl.⁷ ................................ A61K 7/16
(52) U.S. Cl. .......................... 424/49; 424/50
(58) Field of Search ................... 424/49, 50; 514/222.2

(56) References Cited

FOREIGN PATENT DOCUMENTS

| DE | 2618666 | | 11/1976 |
| EP | 0 139 534 | * | 2/1985 |
| EP | 0139534 | | 5/1985 |
| EP | 0521225 | | 1/1993 |
| GB | 1557163 | * | 12/1979 |

OTHER PUBLICATIONS

Carranza F. Glickman's Clinical Periodontology, W. B. Saudners Co., Phila. pp. 196–197, 137–138, 1979.*
Zimmermann M. The Antimicrobial Actions of Taurolin and Other Preparations on the Pathogenic Spectrum in Dentoalveolar Infections. Int J of Clinical Pharm, Therapy and Toxicology. 31(3)130–136, 1993.*
Zimmermann et al., "In vitro activity of taurolidine, chlorophenol–camphor–menthol and chlorhexidine against oral pathogenic microorganisms," *Arzneimittel–Forschung Drug Research*, 42(II):9, pp. 1157–1159, (1992).
Zimmermann et al., "The antimicrobial actions of Taurolin and other preparations on the pathogenic spectrum in dentoalveolar infections," *Int. J. Clinl. Pharmacol. Ther. Toxicol.*, 31:3, pp. 130–136, (1993).
Nentwig et al., "Erste klinische Erfahrugen mit Taurolin–Feingranulat in der zahnärztlichen Chirurgie", *zur antimikrobiellien Chemotherapie chirurgischer Infektion*, Chapter 43, pp. 287–289, (1985).
Nentwig et al., "Zur Behandlung postchirurgischer Knochenifektionen," *Fortschr. Kiefer Gesichtschir.*, 30: pp. 35–37, (1985).
S. Reynolds et al., "Taurolin As An Oral Rinse I. Antimicorbial Effects In vitro and In vivo", *Clinical Preventive Dentistry*, 13:2, pp. 13–22, (Mar./Apr. 1991).

* cited by examiner

*Primary Examiner*—Ralph Gitomer
(74) *Attorney, Agent, or Firm*—Rothwell, Figg, Ernst & Manbeck

(57) ABSTRACT

A method of therapeutic treatment of an area of severe infection of soft tissue within or surrounding a tooth of a patient involves administering Taurolidine, Taurultam or mixtures thereof to the area of severe infection.

17 Claims, No Drawings

TREATMENT OF DENTOALVEOLAR INFECTIONS WITH TAUROLIDINE AND/OR TAURULTAM

The present application is a continuation of U.S. Ser. No. 08/770,127, filed Dec. 19, 1996, now abandoned which is a continuation of U.S. Ser. No. 08/374,722, filed Feb. 15, 1995, abandoned, which is a §371 of PCT/GB93/01607, filed Jul. 29, 1993.

The present invention is concerned with the combatting tooth and gum infections, in particular severe dental infections which are located within the alveolar region of the jaw.

Oral infections remain a relatively common cause of pain and discomfort to many patients and combatting such infections thus continues to be of clinical importance.

It was originally believed that the primary cause of dentoalveolar infection was a simple combination of Gram positive and Gram negative aerobic bacteria. Improvements in microbiological techniques have however now led to the realisation that such conditions are in fact usually caused by a mixed aerobic/anaerobic bacterial population, with Gram negative anaerobes playing an important part in the polymicrobial process.

The complex aetiology of oral infections results in the observation of widely variable resistance patterns following administration of conventional oral antibacterial preparations. Such preparations may also not be sufficiently active against some of the pathogenic organisms present. There is thus a need for a wide-spectrum agent to treat such mixed infections. Administration of an agent which is ineffective against some of the bacteria present will result in proliferation of the resistant bacterial species and complete elimination of the infection may not be achieved. Typically, the types of bacteria present in dentoalveolar infections include aerobes such as *Streptococcus viridans* qr., Streptococcus gr C., Corynebacterium spy., Neisseria spp and *Haemophilus influenzae*. Anaerobes which are also commonly present include Peptococcus spp:, Bacteroides spp. and Furobacterium spp.

Conventional treatments include bactericidal agents such as chlorphenol-camphor-menthol, chlorhexidine and antibiotics such as chlorteracyclin and tetracinolon. However such agents are not without unpleasant side-effects including allergic reactions, toxic tissue reactions causing inflammation and necrosis, tooth or filling discoloration and affecting the senses of taste and smell. Moreover, conventional agents require a relatively prolonged period of treatment to be completely effective.

The use of Chlortetracycline and Democlocycline is considered inadvisable because of their instability and increased toxicity. It has been shown in this connection, that formation of the highly nephro-toxic anhydro-4-epitetracyclin-hydrochloride occurs in older Tetracycline preparations.

The aminoglycoside antibiotic Neomycin may only be applied locally because of its extreme nephrotoxic, ototoxic and muscle relaxant properties. In this context, it is to be noted that resorption can occur when the ectoderm is damaged (i.e. marginal and apical parodontitis, mucous-membrane ulceration) and repeated usage can lead to analogous side-effects. Because of multiple resistant germ strains and an allergy rate of 15–30%, the withdrawal of this preparation was suggested in 1975. The quinoline derivative Aminoquinuride (Surfen), which increases the spectrum of Neomycin, has not been investigated sufficiently and its effectivity is controversial.

Synthetic corticosteroid derivatives like Prednisolone and Triamcinolone are intended to supercede the role of an analgesic in combination preparations. Although their strong anti-inflammatory and anti-allergic properties make for a quick reduction of pain this would always be accompanied by an immune separation which arises out of a comprehensive inhibition mesenchymal reaction. As well as an inhibition of the lympho-reticular system, damage also arises to the DNA-repair and mitosis capability which can lead to tissue atrophy. The fibrinogen concentration in the plasma is reduced by simultaneously strengthened fibrinolysis. It has been shown that the slow release of the working substance due to the insolubility of glucocortoid, conceals the danger that it will exhaust the efficacy of antibiotic too soon and thereby the infection could either spread unrestrained, or develop into a chronic condition. The unpleasant taste of prednisolone has also proved a deterrant against its use.

Although Chlorophenol-Camphor and Chlorophenol-Camphor-Menthol solutions are often recommended for root canal instillation and no significantly higher or stronger pain sensation following instillation in the pulpen cavity has been reported as against comparative clinical experiments, the high toxic potential is undisputed. In animal experiments strong tissue toxic reactions have been observed in the form of inflammation and necrosis formation.

Chlorhexidine, which has proved itself in extensive experimental and clinical studies as a broad spectrum anti-microbial, is also cell damaging. In tests carried out on human desmodontal fibroblasts, accelerated ageing and a cytopathological effect were demonstrated. The release of p-chloroaniline as a possible by-product of chlorhexidine, which is suspected of causing mutation and of being carcinogenic, is often denied.

It has now been found that taurolidine is effective against oral infections, especially those that are located within the infrastructure of the jaw, but exhibits a much reduced level of side-effects and provides effective relief in a shorter period.

Additionally, administration of suitable taurolidine containing compositions will neutralise bacterially originating endo- and exo-toxins as well as attacking the bacteria themselves.

Taurolidine is a synthetic derivative of the naturally occurring 2-aminoethane sulphonic acid, taurine. The use of taurolidine as a potential anti-microbial substance, acting by a methylol transfer mechanism, has been disclosed in GB 1,124,285. It is sold by Ed. Geistlich Sohne AG. under the registered Trade Mark 'Taurolin'. The antibacterial substance taurultam is closely related to taurolidine and, indeed, is formed during the methylol transfer reaction between taurolidine and target substances. It is also produced by Ed. Geistlich Sohne AG. Taurultam is slightly more water soluble than taurolidine but possesses fewer methylol transfer groupings.

Taurolidine and taurultam containing toothpastes, toothgels and mouthwashes have also been disclosed in GB 1557163 and it was suggested that such formulations could be used generally in dental care, but were particularly useful in the treatment of parodontosis (a degenerative, non-inflammatory condition of the gums (periodontium) surrounding the teeth which can, result in the destruction of the tissues). The treatment of alveolitis (an infection located within a tooth socket) using a taurolidine gel fine granulate has also been proposed (see Nentwig et al., "Erste klinische Erfahrung mit Taurolin-Feingranulat in der zahnärztlichen Chirugie" in Taurolin-Ein neues Konzept zur antimikrobiellen Chemotherapie chirurgischer Infektion ed. Brückner, 1985, pages 287–289).

However, it was not previously appreciated that taurolidine compositions would be useful in combatting other, more severe dental infections such as gangrene, parodontitis and abscesses. Neither was it known that administration of a taurolidine composition was so much more effective as regards reducing the length of time and the dosage required for treatment.

Thus, the present invention provides the use of taurolidine and/or taurultam in the preparation of an orally acceptable medicament for combatting severe dental infections or dental infection following dental surgery.

The term "combatting" as used herein includes both therapeutic and prophylactic treatment. The term "severe dental infections" is used herein to refer to those infections which have become established in the interior of the jaw infrastructure, eg. dentoalveolar infections, such as gangrene, parodontitis or dental abscesses.

The condition parodontitis (or periodontitis) is an inflammatory reaction of the tissues surrounding a tooth and can be characterised by formation of periodontal pockets, pus formation, bone resorption, destruction of the periodontal ligament and tooth loss. Parodontitis is a different condition from parodontosis.

One advantage of this aspect of the invention is that the long term pain (toothache) is more rapidly reduced as compared with other antibacterial treatments. This is thought to be due to direct action of the active compounds on tumour necrosis factor (TNF), which is the cytokine responsible for many pain reactions.

It has also been found that taurolidine and/or taurultam can be used prophylactically following surgery such as implantation.

Dental, mandibular or maxillofacial surgery is relatively common and varies from a complete restructing of the jaw bone, (for example following injury to that area) to replacement of a natural tooth with an artificial dentiform implant (false tooth). Removal of a natural tooth may have occurred by accident, for example resulting from a blow to the face, or may be undertaken by surgical techniques made necessary by, for example, untreated decay of the tooth structure. Where a false tooth is to be inserted, the tooth socket is generally prepared by the dental surgeon. Usually a titanium implant is first located in the tooth socket, and then the false tooth proper is firmly attached to the titanium implant, conveniently by means of opposing screw threads so that the false tooth may be simply screwed into place. However, there is a high incidence of post-operative infection which can cause the patient much pain and discomfort, but more seriously can also lead to the ultimate rejection of the implant. Infection is a particular problem in the mouth since mixed populations of endogenous bacteria are always present and consumption of fresh food inevitably leads to the introduction of bacteria into the mouth.

Moreover it is virtually impossible to sterilise the mouth for sustained periods of time and the moist, warm conditions are ideal for bacterial reproduction.

It has however now been found that taurolidine and/or taurultam can be used prophylactically, for example by simple local application, to greatly reduce the incidence of post-operative infection.

The present invention thus provides the use of taurolidine and/or taurultam in the preparation of an orally acceptable prophylactic medicament to prevent dental or gum infections, and in particular to prevent such infections following dental, mandibular or maxillofacial surgery.

Particularly suitable compositions of taurolidine and/or taurultam which may be used to combat severe dental infections (as defined above) or as a prophylaxis include gels, emulsions, liquid gel or rinse solutions.

Certain of these compositions are new and comprise a further aspect of the present invention.

One particular formulation for use in combatting tooth infections is an aqueous emulsion comprising taurolidine or taurultam in solution in the aqueous phase. The oily phase of such an emulsion can comprise a physiologically acceptable oil eg. a food oil such as soya or arachis oil. One or more emulsifiers can be present, for example non-ionic emulsifiers such as glyceryl monostearate, fatty alcohols such as cetyl or myristyl alcohol, or lecithin. A thickening agent such as hydroxyethylcellulose (Natrosol 250 HHR), carboxymethylcellulose, polyethylene glycol, sodium alginate, polyacrylic acid cross-linked by an alkyl ether of pentaerythritol or sucrose (Carbopol) or polyvinylpyrolidone is desirably added. The advantage of such a formulation is delayed release of the taurolidine or taurultam when the formulation is introduced in the vicinity of the infection and resistance to elimination from the site of infection by saliva.

Accordingly, the present invention further provides an orally acceptable composition, said composition comprising taurolidine and/or taurultam together with pharmaceutically acceptable excipients in the form of a liquid gel, rinse solution or as an emulsion. These compositions according to the invention may be used either by themselves or in conjunction with surgery to combat the infection.

One particularly useful aspect is the impregnation of a gauze strip with a taurolidine and/or taurultam-containing emulsion which can be applied to the affected area by the dentist or orthodontist.

A taurolidine and/or taurultam containing gel is particular convenient for prophylactic use. A tube of the gel can be given to the patient who will then apply it to the affected area, as required, for example up to 6 times a day, depending on the extent of surgery and the strength of the gel.

Typically, an orally acceptable composition according to the present invention will comprise 0.5 to 5% taurolidine by weight, preferably 1 to 3% by weight, or 0.75 to 7.5% by weight of taurultam, preferably 1.5 to 4.5%.

The invention further provides a method of combatting severe dental infections (as defined herein), said method comprising administering an orally acceptable taurolidine and/or taurultam-containing composition to the affected area of the patient.

According to a particular feature of the invention we provide the use of taurolidine and/or taurultam for combatting severe dental infections such as parodontitis, dental gangrene or abscesses and for the manufacture of dental compositions for such treatment.

The liquid compositions of the invention are particularly adapted for combatting dentoalveolar infections, such as gangrene or abscesses, for example by introduction via a syringe into tooth canals or application at or near the site of infection for delayed release. Such liquid compositions include emulsions, as indicated hereinafter, which may be applied via an impregnated gauze strip overlying the infected area, as well as rinse solution which can be used in the treatment of gangrene, abscesses and perikornitis and liquid dental gels which can be introduced via a syringe in the treatment of gangrene, apical astitis and root canal treatment.

Taurolidine has been tested for a number of orodental indications against therapy using conventional antibacterials. It could be seen that all target variables fell significantly more quickly under taurolidine medication than under conventional therapy. The total treatment time in the standard group was about 40% longer than in the taurolidine group. Moreover significantly less antibiotics and analgetics were required under taurolidine medication than under standard therapy. In contrast to most of the conventional preparations, which implicate a lot of side effects as irritation of smell and taste, discoloring of teeth and fillings, allergic reactions and histotoxicity with consecutive necroses, taurolidine only shows slight pain for some minutes after application during the acute period or inflammation.

The following study clearly demonstrates that treatment of severe dental infections using taurolidine compositions results in a marked decrease in the length of treatment time.
Comparison of Taurolidine and Conventional Treatments for Dentoalveolar Infections
Material and Methods The in-vivo tests were carried out at the Clinic for Maxillofacial Surgery, Munich University between 1989 and 1992. In accordance with modern biometric principles the study was planned as a controlled clinical trial, i.e. it was conducted according to a prospective, protective, randomized, monocentre and simple blind design.
Indications The following 6 indications examined were selected specifically on the basis of their incidence and clinical relevance.
Alveolitis sicca dolorose
Gangrene
Parodontitis marginalis
Pericoronitis
Abscess
Infection Prophylaxis
Test Preparations The test substances investigated were 4 different galenic presentation forms of the active component taurolidine and 4 conventional finished pharmaceuticals.

Taurolidine$^R$ irrigation fluid 3% (Geistlich, Wolhusen/Switzerland) (1 ml cont.: 30 mg taurolidine, 50 mg PVP 17)

Taurolidine$^R$ liquid gel 3% (Geistlich, Wolhusen/Switzerland (1 g cont.: 30 mg taurolidine, hydroxycellulose)

Taurolidine$^R$ dental emulsion 3% (Geistlich, Wolhusen/Switzerland) (1 g cont.: 30 mg taurolidine, fatty acid triglyceride, lecithin)

Taurolidine$^R$ dental gel 2% (Geistlich, Wolhusen/Switzerland (1 g cont.: 20 mg taurolidine, hydroxycellulose, gluside, polysorbates)

AUREOMYCIN$^R$ ointment 3% (Cynamid-Novalis, Wolfratschausen/FRG) (1 g cont.: 30 mg chlorotetracycline, vaseline-anhydrous lanolin)

DONTISOLON$^R$ ointment Type M (Hoechst, Frankfurt Germany) (1 g cont.: 5 mg prednisolone, 2 mg neomycin HCL, 3 mg aminoquinuride 2HCl 3.5 $H_2O$, excipients)

CHKM$^R$ solution (Haupt, Wurzburg/Germany) (1 ml cont.: 295 mg p-chlorophenol, 767 mg camphor, 18 mg menthol)

CHLORHEXAMED$^R$ dental gel 1% (Blend-a-med, Mainz/Germany) (1 g cont.: 10 mg chlorhexidine digluconate, excipients).
Therapy Regimens For each of the 6 indications investigated an exact therapeutic procedure was fixed. The surgical management was carried out according to the individual situation in the usual manner. Tables 1 and 2 show the antimicrobial therapy regimens defined for patient groups A (Taurolidine group) and B (Standard group). It is evident, that the only difference, with the same quantity of substance applied in the same form, was the choice of preparation.

TABLE 1

THERAPY REGIMEN PATIENT GROUP A

| DIAGNOSIS | PREPARATION | QUANTITY | APPLICATION |
|---|---|---|---|
| ALVEOLITIS | T-Irrigation fluid 3% | 3.0 ml | Irrigation |
|  | T-Dental emulsion 3% | 0.5–1.0 g | Strip-charging or local application |
| GANGRENE | T-Irrigation fluid 3% | 3.0 ml | Irrigation |
|  | T-Liquid gel 3% | 0.05–0.1 g | Canal instillation |
| PARODONTITIS | T-Liquid gel 3% | 0.1–0.2 g | Sulcus instillation |
|  | T-Dental emulsion 3% | 0.5–1.0 g | Sulcus instillation |
| PERICORONITIS | T-Irrigation fluid 3% | 3.0 ml | Irrigation |
|  | T-Dental emulsion 3% | 0.5–1.0 g | Strip-charging or local application |
| ABSCESS | T-Irrigation fluid 3% | 3.0 ml | Irrigation |
|  | T-Dental emulsion 3% | 0.5–1.0 g | Strip-charging or local application |
| INFECTION PROPHYLAXIS | T-Dental get 2% | 1.0–2.0 g | Local application |

T represents "Taurolin" in the Table above.

TABLE 2

THERAPY REGIMEN PATIENT GROUP B

| DIAGNOSIS | PREPARATION | QUANTITY | APPLICATION |
|---|---|---|---|
| ALVEOLITIS | NaCl Solution 0.9% | 3.0 ml | Irrigation |
|  | AUREOMYCIN Ointment 3% | 0.5–1.0 g | Strip-charging |
| GANGRENE | $H_2O_2$ Solution 3% | 3.0 ml | Irrigation |
|  | CHKM Solution | 0.05–0.1 g | Canal instillation |
| PARODONTITIS | DONTISOLON Ointment M | 0.1–0.2 g | Sulcus instillation |
| PERICORONITIS | NaCl Solution 0.9% | 3.0 ml | Irrigation |
|  | AUREOMYCIN Ointment 3% | 0.5–1.0 g | Strip-charging |
| ABSCESS | NaCl Solution 0.9% | 3.0 ml | Irrigation |
|  | AUREOMYCIN Ointment 3% | 0.5–1.0 g | Strip-charging |
| INFECTION PROPHYLAXIS | CHLORHEXAMED Dental gel 1% | 1.0–2.0 g | Local application |

Investigated Parameters and Randomization

For critical examination of the effectiveness of the different pharmaceuticals concerning therapeutic success and total treatment time clinical parameters reflecting the progress of recovery were controlled and documented at every session. The following 6 target variables were defined and evaluated by a uniform scale (0=none to 4=very strong):
Pain
Swelling
Secretion
Pressure pain
Repercussion
Remission Progress of Therapy As is evident from Table 3 all target variables fell more quicker under taurolidine medication than under conventional therapy. For example it can be seen that those patients who were treated with taurolidine were pain-free an average of 2 days earlier than those under conventional treatment. All results were statistically highly significant in Wilcoxon-Mann-Whitney U-test ($p<0.0001$).

TABLE 3

| | TARGET VARIABLES | | | | | | | | | |
|---|---|---|---|---|---|---|---|---|---|---|
| | PAIN | | SWELLING | | SECRETION | | PRESSURE PAIN | | PERCUSSION | |
| | TIME (days) | | | | | | | | | |
| | TAUR | STAN | TAUR | STAN | TAUR | STAN | TAUR | STAN | TAUR | STAN |
| | n (total) | | | | | | | | | |
| | 600 | 600 | 600 | 600 | 600 | 600 | 600 | 600 | 600 | 600 |
| Minimum | 1 | 1 | 1 | 1 | 1 | 1 | 1 | 1 | 1 | 1 |
| Maximum | 14 | 21 | 14 | 24 | 15 | 18 | 15 | 18 | 13 | 17 |
| Mean | 53 | 7.3 | 4.5 | 6.2 | 3.9 | 5.0 | 5.3 | 7.3 | 1.9 | 2.4 |
| STD DEV | 2.3 | 3.0 | 2.5 | 3.5 | 2.5 | 3.5 | 2.3 | 2.9 | 1.9 | 2.8 |
| P (U-Test) | <0.0001 | | <0.0001 | | <0.0001 | | <0.0001 | | <0.0001 | |

The score-level 5 (total) was given at the moment of complete remission and describes consequently the final point of treatment.
As modifying variables were recorded:
Age, sex, optional analgetic and antibiotic application as well as the site of lesion.

200 cases were treated in each indication group, the total number amounted to 1,200. The distribution into the two therapy regimens was realised by random sampling. Statistical evaluations were made by means of testing methods described in customary literature.
Results The homogeneity tests carried out showed no statistically differences whatever ($p>0.05$), that is the comparability of the two patient groups was guaranteed.
Characterisation of Patients The patients ranged between 1 and 89 years of age, with a mean of 38.7 years (Standard deviation STD DEV=±16.3). As was expected, stratification according to the indications showed moderate fluctuation (Pericoronitis with a mean of 29.4 years to parodontitis with a mean of 43.5 years).

The distribution of the sexes showed men (57.3%) to be in a small majority and this trend was the same across all indication groups. At first this fact seems to be astonishing, but it is in accordance with the total sex distribution in our clinic patients, which exhibits 54.5 males vs. 45.5% females (1991). The localisation of the lesions corresponded to the experiences in dental medicine. Alveolitis sicca dolorosa (67.5%) and pericoronitis (90.5%) mostly occurred in the lateral part of the mandible, while the other indications were well distributed between upper and lower jaw.

Both antibiotics as well as analgetics had been administered more often in the standard group than in the taurolidine group. The differences were statistically significant ($p=0.007$ resp. $p=0.01$).

Total Treatment Time

Tables 4 and 5 show the course of the remission for the two therapy regimens. A superior effectiveness of taurolidine to the standard therapy was demonstrable for all 6 indications corresponding to a clinical relevant more rapid recovery ($p<0.0001$). Furthermore it is striking that the standard deviations in the taurolidine group were generally smaller than the comparable values in the standard group. This is also a fact that allows the dentist a better estimation of the required treatment time. Any influence of the investigated modifying variables as age, sex, localisation of the lesion and optional antibiotic or analgetic administration on the process of recovery as well as on total treatment time could not be shown neither in the taurolidine nor in the standard group.

TABLE 4

| | DIAGNOSIS | | | | | |
|---|---|---|---|---|---|---|
| | ALVEOLITIS | | GANGRENE | | PARODONTITIS | |
| | TIME (days) | | | | | |
| | TAUR. | STAN-DARD | TAUR. | STAN-DARD | TAUR. | STAN-DARD |
| | n (total) | | | | | |
| | 100 | 100 | 100 | 100 | 100 | 100 |
| Minimum | 3 | 3 | 2 | 3 | 2 | 3 |
| Maximum | 15 | 18 | 10 | 24 | 14 | 15 |
| Mean | 5.6 | 8.2 | 5.0 | 7.7 | 5.1 | 6.4 |
| STD DEV | 2.5 | 3.2 | 18 | 3.7 | 2.1 | 2.2 |
| P (U-Test) | <0.0001 | | <0.0001 | | <0.0001 | |

TABLE 5

| | DIAGNOSIS | | | | | |
|---|---|---|---|---|---|---|
| | PERICORONITIS | | ABSCESS | | INFECT. PROPHYLAXIS | |
| | TIME (days) | | | | | |
| | TAUR. | STAN-DARD | TAUR. | STAN-DARD | TAUR. | STAN-DARD |
| | | | n (total) | | | |
| | 100 | 100 | 100 | 100 | 100 | 100 |
| Minimum | 2 | 3 | 2 | 3 | 3 | 5 |
| Maximum | 12 | 18 | 13 | 16 | 13 | 16 |
| Mean | 5.1 | 7.3 | 5.5 | 7.7 | 7.5 | 10.0 |
| STD DEV | 1.9 | 2.9 | 2.1 | 2.8 | 1.8 | 2.3 |
| P (U-Test) | <0.0001 | | <0.0001 | | <0.0001 | |

The invention is further illustrated by the following, non-limiting Examples.

EXAMPLE 1

| 3% Taurolidine Dental Emulsion Preparation of 4.0 kg | | | |
|---|---|---|---|
| Composition: | | | % (by weight) |
| A | Egg lecithin | | 5.00 |
| | Distilled water | | 46.00 |
| B | Distilled water | | 24.00 |
| | Natrosol 250 HHR | | 0.50 |
| C | Taurolidine | | 1.00 |
| D | Glycerylmonostearate | | 5.00 |
| | Soya oil | | 10.00 |
| E | Oleum Menthae Supramint BP | | 0.30 |
| F | Taurolidine (micronised) | | 2.00 |
| | Distilled water | | 6.20 |
| | | | 100.00 |

Preparation
A Dissolve with stirring;
B disperse completely with stirring;
C add to A and dissolve;
B add to A/C and homogenise. Heat to 70° C.;
D mix with heating to 70° C.;
 add the fatty phase to the aqueous phase in an emulsifying device and emulsify;
 cool with stirring to 25° C.;
add and mix in;
disperse and add to the product; homogenise again.

EXAMPLE 2

| 3% Taurolidine Dental Emulsion | | |
|---|---|---|
| Composition: | | % (by weight) |
| A | Egg lecithin | 5.00 |
| | Distilled water | 43.00 |
| B | Distilled water | 22.00 |
| | Kollidon 17 PF | 5.00 |
| | Natrosol 250 HHR | 0.50 |
| C | Taurolidine | 1.00 |
| D | Glycerylmonostearate | 5.00 |
| | Soya oil | 10.00 |
| E | Oleum Menthae Supramint BP | 0.30 |
| F | Taurolidine (micronised) | 2.00 |
| | Distilled water | 6.20 |
| | | 100.00 |

Preparation

A Dissolve with stirring;
B disperse completely with stirring;
C add to A and dissolve;
B add to A/C and homogenise. Heat to 70° C.;
D mix with heating to 70° C.;
 add the fatty phase to the aqueous phase in an emulsifying device and emulsify;
 cool with stirring to 25° C.;
E add and mix in;
F disperse and add to the product; homogenise again.

EXAMPLE 3

| 3% Taurolidine Dental Emulsion | | |
|---|---|---|
| Composition: | | % (by weight) |
| A | Egg lecithin | 5.00 |
| | Distilled water | 43.00 |
| B | Distilled water | 22.00 |
| | PEG 4000 | 5.00 |
| | Natrosol 250 HHR | 0.50 |
| C | Taurolidine | 1.00 |
| D | Glycerylmonostearate | 5.00 |
| | Soya oil | 10.00 |
| E | Oleum Menthae Supramint BP | 0.30 |
| F | Taurolidine (micronised) | 2.00 |
| | Distilled water | 6.20 |
| | | 100.00 |

Preparation

A Dissolve with stirring;
B disperse completely with stirring;
C add to A and dissolve;
B add to A/C and homogenise. Heat to 70° C.;
D mix with heating to 70° C.;
 add the fatty phase to the aqueous phase in an emulsifying device and emulsify;
 cool with stirring to 25° C.;
E add and mix in;
F disperse and add to the product; homogenise again.

EXAMPLE 4

3% Taurolidine Dental Emulsion

| | Composition: | % (by weight) |
|---|---|---|
| A | Egg lecithin | 5.00 |
| | Distilled water | 43.00 |
| B | Distilled water | 22.00 |
| | PEG 20,000 | 5.00 |
| | (and higher up to 100,000) | |
| | Natrosol 250 HHR | 0.50 |
| C | Taurolidine | 1.00 |
| D | Glycerylmonostearate | 5.00 |
| | Soya oil | 10.00 |
| E | Oleum Menthae Supramint BP | 0.30 |
| F | Taurolidine (micronised) | 2.00 |
| | Distilled water | 6.20 |
| | | 100.00 |

Preparation

A Dissolve with stirring;
B disperse completely with stirring;
C add to A and dissolve;
B add to A/C and homogenise. Heat to 70° C.;
D mix with heating to 70° C.;
  add the fatty phase to the aqueous phase in an emulsifying device and emulsify;
  cool with stirring to 25° C.;
E add and mix in;
F disperse and add to the product; homogenise again.

EXAMPLE 5

3% Taurolidine Dental Emulsion

| | Composition: | % (by weight) |
|---|---|---|
| A | Egg lecithin | 5.00 |
| | Distilled water | 43.00 |
| B | Distilled water | 24.00 |
| | Natrosol 250 HHR | 0.50 |
| C | Taurultam | 4.5 |
| | Distilled water | 4.7 |
| D | Glycerylmonostearate | 8.00 |
| | Soya oil | 10.00 |
| E | Oleum Menthae Supramint BP | 0.30 |
| | | 100.00 |

Preparation

A Dissolve with stirring;
B completely disperse with stirring;
C dissolve and add to A;
B add to A/C and homogenise. Heat to 70° C.;
D mix with heating to 70° C.;
  add the fatty phase to the aqueous phase in an emulsifying device and emulsify;
  cool with stirring to 25° C.;
E add and mix in.

EXAMPLE 6

Taurolidine Liquid Dental-Gel 2%

| Composition: | % (by weight) |
|---|---|
| Taurolidine | 2.00 |
| Lidocaine HCl | 2.00 |
| Edible gelatin S 08.080 | 0.30 |
| Natrosol 250 HHR | 0.75 |
| Carbopol 941 | 0.75 |
| Distilled water | 91.15 |
| Saccharine solution 10% | 0.40 |
| Tween 20 | 0.80 |
| Tween 80 | 1.60 |
| Oleum Menthae Supramint BP | 0.25 |
| KOH 50% ig | pH 7.2 |
| | pH 7.20 |

Preparation

Dissolve taurolidine, lidocaine and edible gelatin in water with warming;
cool to ambient temperature;
add the natrosol and homogenise;
add the carbopol and disperse;
allow to fully swell with stirring;
add saccharine solution;
mix the Tweens and Oleum Menthae and add;
adjust the pH with KOH.

What is claimed is:

1. A method of therapeutic treatment of an area of severe inflammation associated with severe infection of soft tissue within or surrounding a tooth of a patient, wherein said severe inflammation is a result of severely infected tissue having a condition selected from the group consisting of severely infected soft tissue within said tooth, periodontitis marginalis in soft tissue surrounding said tooth, and dental abscesses in soft tissue surrounding said tooth, said method comprising administering an orally-acceptable member selected from the group consisting of Taurolidine, Taurultam and mixtures thereof to said area of severe inflammation associated with severe infection of said soft tissue, in conjunction with or following dental surgery of said patient, so as to treat said inflammation.

2. A method of therapeutic treatment of an area of severe infection of soft tissue within a tooth of a patient, said method comprising administering an orally-acceptable member selected from the group consisting of Taurolidine, Taurultam and mixtures thereof to said area of severe infection of soft tissue within said tooth of a patient, so as to treat said infection.

3. The method of claim 2, wherein said treatment is in conjunction with or following dental surgery.

4. The method of claim 3 wherein said administering comprises instillation of said member in said tooth canal or said root canal.

5. The method of claim 3 wherein said soft tissue is within a tooth canal or root canal of said tooth.

6. The method of claim 5 wherein said severe infection of said soft tissue within said tooth is gangrene.

7. The method of claim 5 wherein said dental surgery is root canal treatment.

8. A method of therapeutic treatment of an area of severe inflammation associated with severe infection of soft tissue surrounding a tooth of a patient, wherein said severe inflammation is a result of severely infected tissue having a condition of periodontitis marginalis, said method comprising administering an orally-acceptable member selected from the group consisting of Taurolidine, Taurultam and mixtures thereof to said area of severe inflammation associated with severe infection of soft tissue surrounding said tooth, in conjunction with or following dental surgery of said patient, so as to treat said inflammation.

9. The method of claim 8, wherein said member is present in a composition which is present in an orally-acceptable gauze strip for therapeutic treatment of severe inflammation associated with severe infection of soft tissue surrounding a tooth, wherein said strip is impregnated with said orally-acceptable composition, said composition including said member selected from the group consisting of Taurolidine, Taurultam and mixtures thereof, together with a pharmaceutically-acceptable excipient, said strip reducing said severe inflammation associated with severe infection when contacted with said soft tissue surrounding said tooth.

10. The method of claim 9, wherein said composition is an emulsion which is applied to said area of severe inflammation by the impregnated strip.

11. The method of claim 8 wherein said severe infection of soft tissue is associated with at least one condition selected from the group consisting of periodontal pockets, pus formation, bone resorption, destruction of periodontal ligament and tooth loss.

12. The method of claim 8, wherein said member is administered solely to said area of severe inflammation.

13. A method of therapeutic treatment of an area of severe inflammation associated with severe infection of soft tissue surrounding a tooth of a patient, wherein said severe inflammation is a result of severely infected tissue having a condition of dental abscesses, said method comprising administering an orally-acceptable member selected from the group consisting of Taurolidine, Taurultam and mixtures thereof to said area of severe inflammation associated with severe infection of soft tissue surrounding said tooth, in conjunction with or following dental surgery of said patient, so as to treat said inflammation.

14. The method of claim 13, wherein said member is present in a composition which is present in an orally-acceptable gauze strip for therapeutic treatment of severe inflammation associated with severe infection of soft tissue surrounding a tooth, wherein said strip is impregnated with said orally-acceptable composition, said composition including said member selected from the group consisting of Taurolidine, Taurultam and mixtures thereof, together with a pharmaceutically-acceptable excipient, said strip reducing said severe inflammation associated with severe infection when contacted with said soft tissue surrounding said tooth.

15. The method of claim 14, wherein said composition is an emulsion which is applied to said area of severe inflammation by the impregnated strip.

16. The method of claim 13 wherein said severe infection of soft tissue is associated with a condition selected from the group consisting of periodontal pockets, pus formation, bone resorption, destruction of periodontal ligament and tooth loss.

17. The method of claim 13, wherein said member is administered solely to said area of severe inflammation.

* * * * *